United States Patent [19]

Ohno et al.

[11] Patent Number: 5,712,391
[45] Date of Patent: Jan. 27, 1998

[54] SILICONE DERIVATIVES, THEIR PRODUCTION AND USE

[75] Inventors: Hiroyuki Ohno; Natsue Kawahara, both of Tokyo; Isaburo Amano, Chiba; Takanao Suzuki, Kanagawa; Koji Chiba, Chiba, all of Japan

[73] Assignee: Chiba Flour Milling Co., Ltd., Mihama-Ku, Japan

[21] Appl. No.: 671,001

[22] Filed: Jun. 28, 1996

[30] Foreign Application Priority Data

Jun. 30, 1995 [JP] Japan .................... 7-165886

[51] Int. Cl.$^6$ ............ C07D 251/00; C07D 251/40; C07D 251/54; C07F 7/04
[52] U.S. Cl. ............ 544/194; 544/196; 544/204; 556/450
[58] Field of Search .................... 544/196, 204, 544/194; 556/450

[56] References Cited

FOREIGN PATENT DOCUMENTS

| 638065 | 3/1962 | Canada . |
| 0 461 071A1 | 12/1991 | European Pat. Off. . |
| 0 502 821A1 | 9/1992 | European Pat. Off. . |
| 2-43263 | 2/1990 | Japan . |
| 5-140320 | 6/1993 | Japan . |
| WO 94/14822 | 7/1994 | WIPO . |

OTHER PUBLICATIONS

Andrianov, et al, Organosilicon oligomers containing symmetric triazine rings, Vysokomolekuliarnye Sodineniya serii A, vol. 16, issue 10, pp. 2255–9, 1974.

Primary Examiner—Mukund J. Shah
Assistant Examiner—Bruck Kifle
Attorney, Agent, or Firm—David G. Conlin; George W. Neuner

[57] ABSTRACT

Disclosed are amino silicone derivatives having triazinyl groups or pyrimidinyl groups bound to amino groups of amino silicones, their production and use, said silicone derivatives being able to gel silicone oil or to increase the viscosity thereof stably and homogeneously, and therefore being useful as bases for cosmetics, pharmaceutical preparations and industrial materials.

17 Claims, No Drawings

SILICONE DERIVATIVES, THEIR PRODUCTION AND USE

The present invention relates to novel silicone derivatives, their production and use.

BACKGROUND OF THE INVENTION

Silicone oil is useful for its heat resistance, lubricity, water repellency, gloss retention, mist prevention, antistatic properties, mold release lubricant, corrosion resistance, chemical stability and safety. Utilizing these properties, silicone oil has hitherto been used as bases of compositions in a wide variety of fields including various industrial materials such as textile treating agents, surface lubricants, water repelling agents, resin modifiers, paint additives, electrical insulating agents, heat media, grease, oil for machinery, foam stabilizers and anti-foam agents, pharmaceutical preparations and cosmetics.

In particular, silicone oil has been used as bases of pharmaceutical preparations and cosmetics because of its safety. Usually, low-viscosity silicone oil having a viscosity of 100 cs or less at room temperature is widely used as the bases because of its improved extensibility, refreshing feeling and high safety. However, for example, when a paste-like or grease-like silicone composition is prepared, it is difficult to obtain a smooth, homogeneous composition in a single system, and low-viscosity silicone oil is easily separated or discharged from the resulting composition, resulting in low stability.

In order to solve the above-mentioned problem of low-viscosity silicone oil, there has been proposed the use of organic materials such as the methods of using fatty acid esters of dextrin as thickeners (see Japanese Patent Unexamined Publication Nos. 62-121764, 62-143970, 62-143971 and 63-159489), the methods of using fatty acid esters of sucrose (see Japanese Patent Unexamined Publication No. 63-235366) and the methods of using trimethylsilylated polyvinyl alcohol or trimethylsilylated polysaccharides (see Japanese Patent Unexamined Publication No. 62-240335), and the use of inorganic materials such as the methods of using organically modified viscosity minerals (see Japanese Patent Unexamined Publication Nos. 62-45656, 62-54759 and 63-72779). However, the use of these organic and inorganic materials as the thickeners results in the problem of deteriorating inherent characteristics of low-viscosity silicone oil such as refreshing feeling and extensibility.

Recently, methods have been proposed in which low-viscosity silicone oil is treated using compounds obtained by partially crosslinking silicones having a specific degree of polymerization as thickeners under shearing force, thereby obtaining homogeneous paste-like silicone compositions (see Japanese Patent Unexamined Publication Nos. 2-43263 and 5-140320). However, these methods require the use of mixers such as ball mills, three-roll mills and colloid mills having strong shearing force for obtaining paste-like silicone compositions, resulting in disadvantages such as troublesome preparation, high viscosity of the resulting compositions and restricted compounding amounts of the compositions. Bases have therefore been desired which can make gel and increase viscosity by simpler compounding without impairing the inherent feeling of low molecular weight silicones having a viscosity of 100 cs or less.

SUMMARY OF THE INVENTION

As a result of intensive investigation under such situations, the present inventors have discovered that novel silicone derivatives in which triazine compounds or pyrimidine compounds are chemically bound to amino groups of amino-modified silicones can gel silicone oil and/or liquid oil or can increase the viscosity thereof simply and stably, thus completing the present invention.

Namely, the present invention provides:

(1) A triazinyl group- or pyrimidinyl group-containing amino-modified silicone derivative having a triazinyl group or a pyrimidinyl group bound to an amino group of an amino-modified silicone, or a derivative in which triazine or pyrimidine is bound to silicone oil;

(2) A triazinyl group- or pyrimidinyl group-containing amino-modified silicone derivative represented by general formula (1), including a silicone derivative in which a triazinyl group or a pyrimidinyl group is chemically bound to silicone oil as represented by general formula (1) irrespective of its raw material:

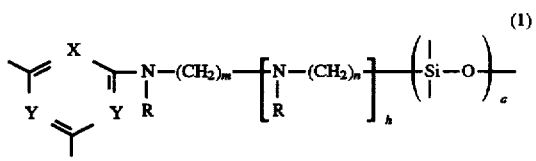

wherein each R, which may be the same or different, represents hydrogen or a linear, branched-chain or cyclic hydrocarbon group of 1 to 8 carbon atoms; m and n each represent integers from 1 to 6; h represents an integer from 0 to 6; "a" represents an integer from 1 to 400; and at least two of Y are nitrogen, and the remainder is carbon;

(3) The silicone derivative described in the above (1), which is represented by general formula (2), or an amino silicone derivative in which a triazine ring or a pyrimidine ring is bound to silicone oil having one amino end group at the amino end thereof:

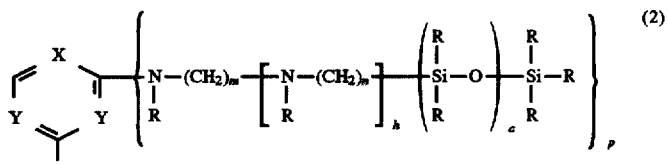

wherein each R, which may be the same or different, represents hydrogen or a linear, branched-chain or cyclic hydrocarbon group of 1 to 8 carbon atoms; m and n each represent integers from 1 to 6; h represents an integer from 0 to 6; "a" represents an integer from 1 to 400; at least two of Y are nitrogen atoms, and the remainder is a carbon atom; p represents an integer from 1 to 3 in the case of triazine, or from 1 to 4 in the case of pyrimidine; and when p is 1 or 2 in the case of triazine, or 1, 2 or 3 in the case of pyrimidine, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon (4) The silicone derivative described in the above (1), which is represented by general formula (3):

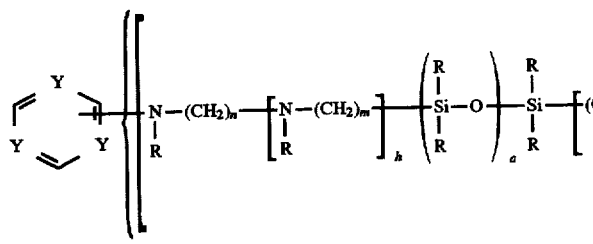 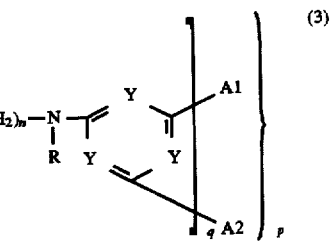

wherein each R, which may be the same or different, represents hydrogen or a linear, branched-chain or cyclic hydrocarbon group of 1 to 8 carbon atoms; m and n each represent integers from 1 to 6; h represents an integer from 0 to 6; "a" represents an integer from 1 to 400; at least two of Y are nitrogen atoms, and the remainder is a carbon atom; q is an integer from 0 to 10; p represents an integer from 1 to 3 in the case of triazine, or from 1 to 4 in the case of pyrimidine; and when p is 1 or 2 in the case of triazine, or 1, 2 or 3 in the case of pyrimidine, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, as well as a hydrogen atom, may be bound to a residual carbon atom of the triazine ring or the pyrimidine ring;

(i) When q is from 1 to 10, A1 and A2 are each represented by general formula (4):

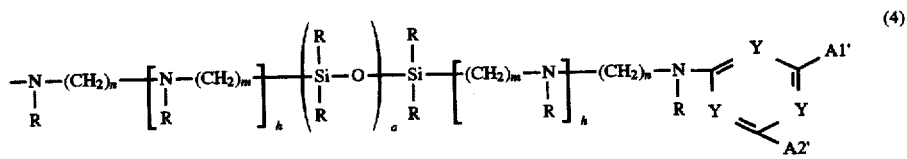

wherein R, m, n, h, a and Y have the same meanings as given above; and A1' and A2' each represent hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms;

or A1 and A2 are each represented by general formula (5):

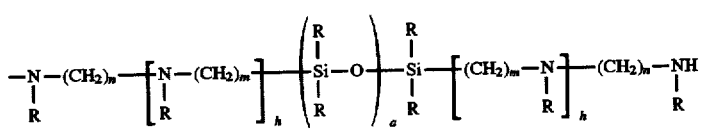

wherein R, m, n, h and a have the same meanings as given above;

or A1 and A2 each represent hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms; and (ii) When q is 0, general formula (3) is represented by general formula (6):

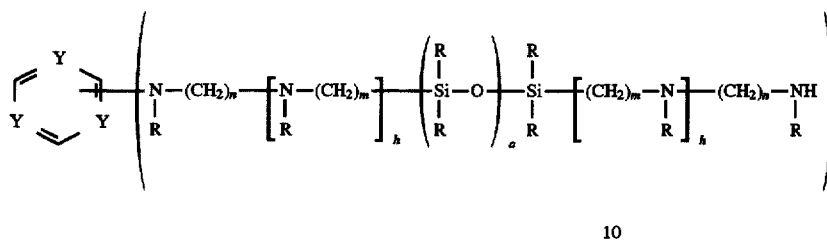

said silicone derivative including a derivative in which 1 to 3 carbon atoms of the triazine ring or 1 to 4 carbon atoms of the pyrimidine ring are bound to α,ω-diamino silicone oil at both amino ends thereof, also including a structure composed of 2 to 10 repeating units thereof which includes a linear, branched and/or network structure, and including a derivative in which one end of the α,ω-diamino silicone oil may be an amino group or an amino group substituted by a linear or branched alkyl group of 1 to 6 carbon atoms without bonding to the triazinyl group or the pyrimidinyl group;

(5) The silicone derivative described in the above (1) represented by general formula (7), which is obtained by allowing a side-chain amino silicone oil to react with a reactive group-containing triazine or pyrimidine compound:

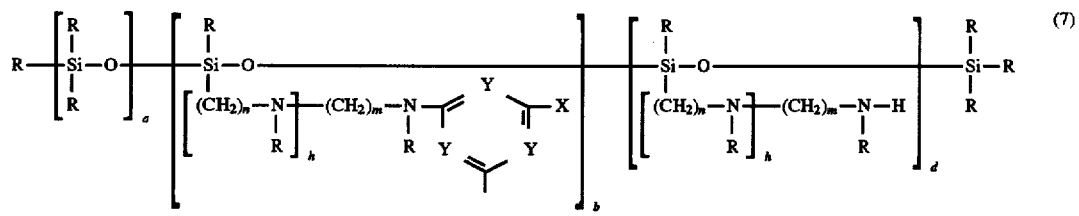

wherein each R, which may be the same or different, represents hydrogen or a linear, branched-chain or cyclic hydrocarbon group of 1 to 8 carbon atoms; m and n each represent integers from 1 to 6; h represents an integer from 0 to 6; "a" and "b" each represent integers of 1 or more, "d" represents an integer of 0 or more, and "a+b+d" represents an integer of 400 or less; "a", "b" and "d" each show the ratios, and do not specify the order of arrangement; and at least two of Y are nitrogen atoms, and the remainder is a carbon atom;

(6) A method for producing the silicone derivative described in the above (1) which comprises allowing a amino silicone oil to react with a reactive group-containing triazine or pyrimidine compound;

(7) The method described in the above (6), in which the amino silicone oil is represented by the following general formula (8):

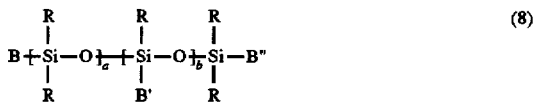

wherein each R, which may be the same or different, represents hydrogen or a linear, branched-chain or cyclic hydrocarbon group of 1 to 8 carbon atoms; a and b each represent integers of 1 or more, and the sum of a and b represents an integer of 400 or less; a and b each show the ratios, and do not specify the order of arrangement; and at least one of B, B' and B" is a group represented by general formula (9):

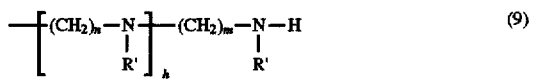

wherein each R', which may be the same or different, represents hydrogen or a linear, branched or cyclic hydrocarbon group of 1 to 8 carbon atoms; m and n each represent integers from 1 to 6; and h represents an integer from 0 to 6; and the reactive group-containing triazine or pyrimidine compound is a compound represented by the following general formula (10):

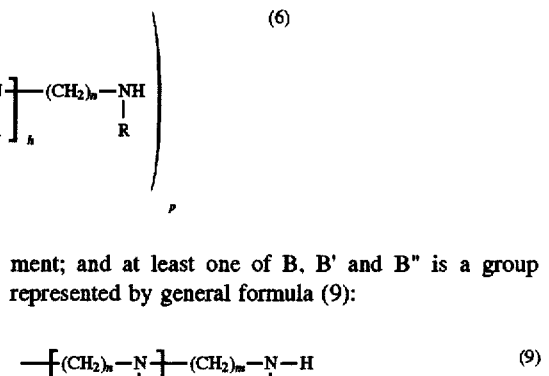

wherein at least one of $X^1$, $X^2$ and $X^3$ represents a halogen atom, the remainders each represent hydrogen atoms, hydroxyl groups, amino groups which may be substituted by linear or branched alkyl groups each having 1 to 6 carbon atoms, carboxyl groups, linear or branched alkyl groups each having 1 to 6 carbon atoms, or linear or branched alkoxyl groups each having 1 to 6 carbon atoms; and at least two of Y are nitrogen atoms, and the other is a carbon atom;

(8) A gelling agent comprising the triazinyl group- or pyrimidinyl group-containing silicone derivative described in the above (1), (2), (3), (4) or (5);

(9) A composition comprising the triazinyl group- or pyrimidinyl group-containing silicone derivative described in the above (1), (2), (3), (4) or (5) and silicone oil and/or liquid oil; and

(10) A base comprising the triazinyl group- or pyrimidinyl group-containing silicone derivative described in the above (1), (2), (3), (4) or (5).

DESCRIPTION OF THE PREFERRED EMBODIMENTS

The present invention will hereinafter be described in detail.

When the novel silicone derivatives of the present invention are produced, in addition to methods in which amino silicone oil is allowed to react with reactive group-containing triazine or pyrimidine compounds as raw materials, methods can be employed in which reactive group-modified silicones having reactive groups such as halogen and amino group-containing triazine or pyrimidine compounds are allowed to react with each other, which has a reversed relationship in the reactive groups with the first method. This is the reason why the silicone derivatives of the present invention include all compounds represented by general formula (1). However, the reactivity of the reactive groups such as halogen on heterocyclic moiety is stronger in the first method, so that the first method is generally used. The first method is hereinafter mainly described, but the second method can also be used similarly.

As the starting materials for producing the novel silicone derivatives of the present invention, the case of using amino silicones is first described. The sites of amino modification may be any of side chains, one end and both ends, and the number of the amino groups, the position thereof, etc. are not limited.

These amino silicones are represented by the following general formula (11):

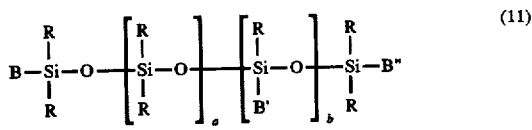

(11)

wherein each R, which may be the same or different, represents a linear, branched-chain or cyclic hydrocarbon group of 1 to 8 carbon atoms; at least one of B, B' and B" is a group represented by general formula (12):

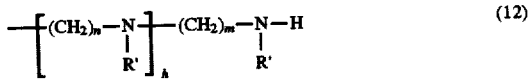

(12)

wherein each R', which may be the same or different, represents hydrogen or a linear, branched or cyclic hydrocarbon group of 1 to 8 carbon atoms, m and n each represent integers from 1 to 6, and h represents an integer from 0 to 6; the remainders of B, B' and B" each represent linear, branched-chain or cyclic hydrocarbon groups each having 1 to 8 carbon atoms; a and b each represent integers of 1 or more, and the sum of a and b represents an integer of 400 or less; and a and b each show the ratios, and do not specify the order of arrangement.

Examples thereof include amino silicones having one amino end group represented by the following general formula (13):

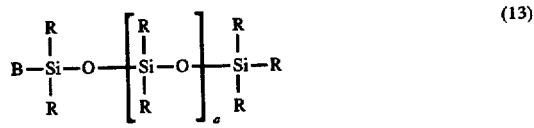

(13)

wherein each R, which may be the same or different, represents hydrogen or a linear, branched-chain or cyclic hydrocarbon group of 1 to 8 carbon atoms; B represents a group represented by general formula (12); and a represents an integer from 1 to 400;

α,ω-diamino silicones represented by the following general formula (14):

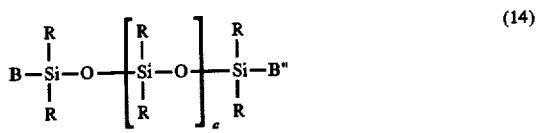

(14)

wherein each R, which may be the same or different, represents hydrogen or a linear, branched-chain or cyclic hydrocarbon group of 1 to 8 carbon atoms; B and B" each represent groups represented by general formula (12); and a represents an integer from 1 to 400; and side-chain amino silicones represented by the following general formula (15):

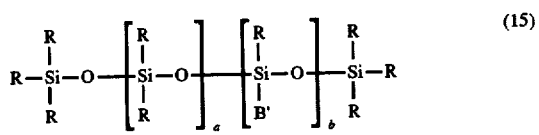

(15)

wherein each R, which may be the same or different, represents hydrogen or a linear, branched-chain or cyclic hydrocarbon group of 1 to 8 carbon atoms; B' represents a group represented by general formula (12); a and b each represent integers of 1 or more, and the sum of a and b represents an integer of 400 or less; and a and b each show the ratios, and do not specify the order of arrangement.

In the compounds represented by general formulas (13), (14) and (15), the amino silicone derivatives used in the present invention, examples of the hydrocarbon groups each having 1 to 8 carbon atoms represented by R include linear hydrocarbon groups such as methyl, ethyl, propyl, butyl, pentyl, hexyl, heptyl and octyl, branched hydrocarbon groups such as isopropyl and isohexyl, alkenyl groups such as vinyl and allyl, cycloalkyl groups such as cyclohexyl and cycloheptyl, and aryl groups such as phenyl and tolyl. These hydrocarbon groups may be substituted by halogen, etc., and examples thereof include 3,3,3-trifluoropropyl. Methyl and phenyl are preferred among others, and methyl is particularly preferred.

In the compounds represented by general formulas (13), (14) and (15), the number of silicon atoms contained in a modified silicone molecule (a+b) is 2 to 400, preferably 10 to 300, and more preferably 40 to 150.

Examples of the amino silicones used in the present invention include the following:

Amino Silicone Oil Manufactured by Dow Corning Toray Silicone Co., Ltd.

Structure (1) (α,ω-diamino silicone)

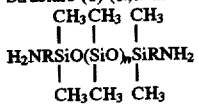

Structure (2) (Side-Chain amino silicone)

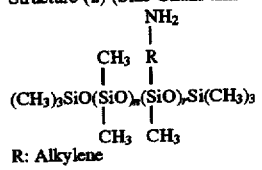

R: Alkylene

| Product Name | Viscosity (cs) | Specific Gravity | Refractive Index | Remarks | NH₂ equivalent |
|---|---|---|---|---|---|
| BY16-853 | 30 | 0.96 | 1.414 | α,ω-diamino silicone | 650 |
| BY16-853B | 80 | 0.97 | 1.407 | α,ω-diamino silicone | 2200 |
| BY16-828 | 120 | 1.05 | 1.453 | side-chain amino silicone | 3500 |
| BY16-850 | 1100 | 0.98 | 1.411 | side-chain amino silicone | 4000 |
| SF8417 | 1200 | 1.07 | 1.452 | side-chain amino silicone | 1800 |
| BY16-849 | 1300 | 1.03 | 1.426 | side-chain amino silicone | 600 |
| BY16-872 | 18000 | 1.01 | 1.421 | side-chain amino silicone | 2000 |
| BX16-755B | 240 | — | 1.408 | secondary amine | 2200 |
| BX16-193 | — | — | — | one amino end group | 4000 |

Amino Silicone Oil Manufactured by Nippon Unicar Co., Ltd.

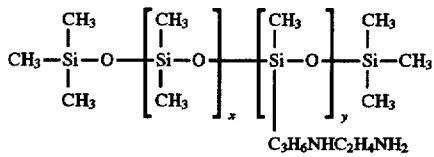

C₃H₆NHC₂H₄NH₂

| Product Name | Amino Equivalent | Si Polymerization Degree |
|---|---|---|
| FZ-3705 | 4,000 | 140 |
| FZ-3707 | 1,400 | 50 |
| FZ-3710 | 1,700 | 300 |
| FZ-3712 | 1,700 | 200 |

The triazine and pyrimidine compounds having reactive functional groups which are used for reaction with the amino silicones are represented by the following general formula (10):

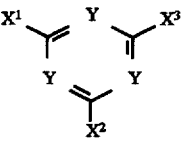  (10)

wherein at least one of $X^1$, $X^2$ and $X^3$ represents a halogen atom, the remainders each represent hydrogen atoms, hydroxyl groups, amino groups which may be substituted by linear or branched-chain alkyl groups each having 1 to 6 carbon atoms, carboxyl groups, linear or branched alkyl groups each having 1 to 6 carbon atoms, or linear or branched alkoxyl groups each having 1 to 6 carbon atoms; and at least two of Y are nitrogen, and the other is carbon.

The reactive groups of these triazine or pyrimidine compounds may be any, as long as they are groups which react with amino groups of the amino silicones. Examples thereof include halogen atoms such as fluorine, chlorine, bromine and iodine. Although substituent groups $X^1$ and $X^2$ of the triazine skeleton may also be any, examples thereof include hydrogen, hydroxyl, amino groups which may be substituted by alkyl groups, halogen, carboxyl, linear or branched alkyl groups each having 1 to 6 carbon atoms, or linear or branched alkoxyl groups each having 1 to 6 carbon atoms. In the amino groups which may be substituted by the alkyl groups, said alkyl groups include linear or branched alkyl groups each having 1 to 6 carbon atoms. Examples of the alkyl-substituted amino groups include ethylamino, propylamino and isopropylamino. Further, the carboxyl groups contain salts thereof such as alkali salts and alkaline earth metal salts, and examples thereof include sodium, potassium, calcium, magnesium, aluminum and zinc salts. Examples of the linear or branched alkyl groups each having

| Amino Silicone Oil Manufactured by Dow Corning Toray Silicone Co., Ltd. | | | | | | |
|---|---|---|---|---|---|---|
| Product Name | Appearance | Viscosity (cs) | Specific Gravity | Refractive Index | Amino Equivalent | |
| SF8417 | light yellowish brown, transparent | 1200 | 0.96 | 1.407 | 1800 | |
| BY16-828 | light yellow, transparent | 120 | 0.96 | 1.414 | 3500 | CH₃ |
| BY16-849 | light yellow, transparent | 1300 | 0.99 | 1.405 | 600 | CH₃ \| CH₃ CH₃ |
| BY16-850 | light yellow, transparent | 1100 | 0.97 | 1.407 | 4000 | \| \| \| \| \| |
| BY16-872 | light yellow, transparent | 18000 | 0.98 | | 2000 | CH₃SiO(SiO)ₐ(SiO)ᵦSiCH₃ |
| | | | | | | \| \| \| |
| | | | | | | CH₃ \| R CH₃ |
| | | | | | | CH₃ \| |
| | | | | | | NH |
| | | | | | | \| |
| | | | | | | R' |
| | | | | | | \| |
| | | | | | | NH₂ |
| BY16-853 | light yellow, transparent | 30 | 0.96 | 1.414 | 650 | CH₃ CH₃ |
| BY16-853B | colorless, transparent | 80 | 0.97 | 1.407 | 2200 | \| \| |
| | | | | | | H₂NR(SiO)ₓSiRNH₂ |
| | | | | | | \| \| |
| | | | | | | CH₃ CH₃ |
| BX16-755B | | 240 | — | 1.408 | | |

R, R': Alkylene

The molecular weight of these amino silicones is 100 to 30,000, preferably 1,000 to 20,000, and more preferably 3,000 to 10,000.

1 to 6 carbon atoms include linear alkyl groups such as methyl, ethyl, propyl, butyl, pentyl and heptyl, branched alkyl groups such as isopropyl, isobutyl, isopentyl and isohexyl, and those of cyclic alkyl groups such as cyclohexyl. Examples of the linear or branched alkoxyl groups each having 1 to 6 carbon atoms include methoxy, ethoxy, propoxy, butoxy, pentaoxy, isopropoxy and dimethoxy.

Examples of these triazine compounds include cyanuric chloride, 2-chloro-4,6-bis(methylamino)-S-triazine, 2-chloro-4,6-bis(ethylamino)-S-triazine (simazine), 2-chloro-4,6-bis(propylamino)-S-triazine, 2-chloro-4,6-bis(butyl-amino)-S-triazine, 2-chloro-4,6-bis(amylamino)-S-triazine, 2-chloro-4-methylamino-6-ethylamino-S-triazine, 2-chloro-4-methylamino-6-propylamino-S-triazine, 2-chloro-4-ethyl-amino-6-isopropylamino-S-triazine (atrazine), 2-chloro-4-ethylamino-6-propylamino-S-triazine, 2-chloro-4-ethyl-amino-6-isobutylamino-S-triazine, 2-chloro-4-propylamino-6-isopropylamino-S-triazine, 2-chloro-4,6-bis(ethoxy)-S-triazine, 2-chloro-4,6-bis(methoxy)-S-triazine, 2-chloro-4,6-bis(propoxy)-S-triazine and 2-chloro-4,6-bis(butoxy)-S-triazine.

Examples of the pyrimidine compounds include 2-chloropyrimidine, 2-chloro-4,6-dimethylpyrimidine, 2-chloro-4,6-(dimethylamino)pyrimidine, 2,5-dichloro-4-methoxy-6-trichloromethylpyrimidine and 2,4,5,6-tetrachloropyrimidine.

On the other hand, in addition to the methods in which the above-mentioned amino silicones are allowed to react with the reactive group-containing triazine or pyrimidine compounds as starting materials, the novel silicone derivatives of the present invention can also be produced by allowing reactive group-containing silicones to react with amino group-containing triazine or pyrimidine compounds. When the reactive group-containing silicones are used, halogen is typically used as the reactive groups. The halogen silicones include, for example, chloro silicone oil and fluoro silicone oil. Examples of the amino group-containing triazine compounds which are allowed to react with the halogen silicone oil include 2,4,6-triamino-s-triazine (melamine), 2,4-diamino-6-dimethyl-s-triazine and 2,4-diamino-6-ethoxy-s-triazine. Examples of the amino group-containing pyrimidine compounds include 2-aminopyrimidine, 2,4-diamino-6-ethyl-5-phenylpyrimidine, 2-amino-4-(2-dibutylaminoethoxy)pyrimidine, 5-(4'-chlorophenyl)-2,4-diamino-6-ethylpyrimidine and 2,4,5,6-tetraaminopyrimidine.

Reaction solvents used in the reaction of these amino silicones with the triazine or pyrimidine compounds or in the reaction of the halogen silicone oil with the amino group-containing triazine or pyrimidine compounds may be any, as long as they dissolve both of them. Such solvents include benzene, toluene, xylene, n-hexane, n-heptane, carbon tetrachloride, chloroform, perchloroethylene, trichloroethylene and chlorobenzene.

The reaction is conducted by dissolving the amino silicone oil or the halogen silicone oil and the triazine compounds or the pyrimidine compounds in the reaction solvents, and heating and adding catalysts if necessary.

The reaction is conducted at room temperature or higher, preferably at 70° to 120° C., and basic compounds such as pyridine, aniline and alkylamines can be used as the reaction catalysts. After the reaction, unreacted halogen groups are substituted by water, alcohols, etc., followed by solvent removal and removal of unreacted products. Then, the resulting products are subjected to vacuum drying to obtain the novel silicone derivatives in which triazinyl groups or pyrimidinyl groups are bound to the amino silicone oil or the halogen silicone oil.

The properties such as gel strength and viscosity can be controlled by changing the binding ratio of the amino silicone to the triazinyl group or the pyrimidinyl group.

For example, when added to liquid oil or silicone oil generally used for cosmetics or pharmaceutical preparations, a di-substituted compound in which silicone oil is introduced into two positions of the triazinyl group or the pyrimidinyl group forms a hard gel, a mono-substituted compound in which silicone oil is introduced into one position forms a soft gel, and a tri-substituted compound in which silicone oil is introduced into all three positions gives a weak gel or a viscosity-increased fluid liquid. With respect to cosmetics, for example, the di-substituted compounds are used for foundations, antiperspirants sticks, mascara, lip sticks and lip cream, the mono-substituted compounds are used for soft gels such as cream, emulsions and cream foundations, and the tri-substituted compounds are used for cosmetic oil and liquid foundations. Further, the di-substituted compounds forming hard gels are used for potting agents for electric and electronic parts and vibration absorbing agents for dampers, and the tri-substituted compounds are used for thickeners, sealing agents and pigment dispersing agents. Thus, any one of the mono-substituted, di-substituted and tri-substituted compounds can be selected depending on the use and the purpose.

Reaction products in which halogen is left cause irritating feeling when they adhere to the skin. They are therefore unsuitable for cosmetics and pharmaceutical preparations. It is therefore preferred that halogen is substituted as described above. However, the reaction products containing halogen can be used for other applications such as water repelling agents, potting agents for electric and electronic parts and vibration absorbing agents for dampers, etc. without any particular problem.

When the amino silicone is an $\alpha,\omega$-diamino silicone or a side chain amino silicone, a compound in which triazinyl or pyrimidinyl groups are bound to all amino groups of the $\alpha,\omega$-diamino silicone or the side chain amino silicone is not dissolved in liquid oil or silicone oil even when it is added thereto, or the resulting gel leads to syneresis in some cases. The reason for this is considered to be that the hard gel is formed by intramolecular or intermolecular crosslinking. A reversible smooth gel can be formed by partially remaining the amino groups uncombined by methods such as appropriate adjustment of the reaction molar ratio, which is deduced to be due to a hydrogen bond.

For example, when the side chain amino silicone has amino groups at 40 positions in a molecule, a gelling agent can be obtained by introducing triazinyl or pyrimidinyl groups into 2 or 3 positions, said gelling agent giving a homogeneous, flexible, soft gel when added to silicone oil having a viscosity of 100 cs or less.

The compounds of the present invention represented by general formula (3) which are obtained by the reaction of the $\alpha,\omega$-diamino silicones with reactive triazine or pyrimidine can be compounds showing fluidity, compounds showing viscosity increasing properties, gel-like compounds or rubber-like elastomers, depending on the reaction conditions such as the reaction molar ratio, the reaction temperature and the reaction time.

For example, when a soft gel is desired, the reaction time is shortened, or the amount of the reactive group-containing triazine or pyrimidine compound is reduced in the reaction. When a harder gel is desired, the reaction time is prolonged, or the amount of the reactive group-containing triazine or pyrimidine compound is increased. Thus, the hardness of product gels can be controlled.

These compounds vary in viscosity according to the degree of polymerization (molecular weight) represented by q in general formula (3), and a higher molecular weight results in a higher viscosity. In addition to this, the linear structure and the crosslinked structure are obtained as the molecular structure according to methods of polymerization. The linear structure results in softer compounds compared with the crosslinked structure. For example, gel-like compounds rich in the linear structure are soft, whereas gels rich in the crosslinked structure become hard, resulting in elastic, rubber-like compounds.

Specifically, the products are described as follows.

When the products are mainly composed of the compounds represented by general formula (3) wherein q is 3 or less, the products are poor in the crosslinked structure and rich in the linear structure. Dissolution thereof in silicone oil results in various compounds extending from high viscous materials exhibiting viscosity increasing properties to weak gel-like compounds.

When the products are mainly composed of the compounds represented by general formula (3) wherein q is 5 to 10, the crosslinked structure is rich, resulting in exhibition of properties extending from weak gel-like properties to hard rubber-like properties.

When the products are mainly composed of the compounds represented by general formula (3) wherein q exceeds 10, the products are almost all composed of the crosslinked structure and further composed of the polymer structure, resulting in exhibition of properties extending from rubber-like properties to resin-like properties.

Similarly to the $\alpha,\omega$-diamino silicones, the compounds of the present invention represented by general formula (7) which are obtained by the reaction of the side-chain amino silicones with reactive triazine or pyrimidine compounds vary in viscosity according to the degree of polymerization (molecular weight) represented by (a+b+d), and a higher molecular weight results in a higher viscosity. For the linear structure and the crosslinked structure developed as the molecular structure according to methods of polymerization, the linear structure results in softer compounds compared with the crosslinked structure. For example, gel-like compounds rich in the linear structure are flexible and soft, whereas gels rich in the crosslinked structure become hard, resulting in elastic, rubber-like compounds.

When cyanuric chloride is used as the triazine compound, it can bind to reactive groups of the silicone at a maximum of 3 positions, because it has 3 reactive groups. The structure of the silicone obtained thereby is apt to take the crosslinked structure, compared with a compound having one reactive group such as 2-chloropyrimidine. The resulting compound has therefore a tendency to become hard.

Further, more amino groups in the molecule of the amino silicone results in more reactive positions, so that the resulting compound is apt to take the crosslinked structure, leading to a hard compound. Accordingly, the use of the silicone having a small amount of amino groups can provide the silicone derivative having desired hardness and properties.

As an example of the specific structure, the side-chain amino silicone is apt to take the intermolecular or intramolecular crosslinked structure when the triazine or pyrimidine compound having at least 2 reactive groups is used, resulting in a hard compound. In order to avoid this problem, the introduction rate of the triazine or pyrimidine compound is decreased, or the triazine compound having one reactive group such as 2-chloro-4,6-bis(ethylamino)-s-triazine or the pyrimidine compound such as 2-chloropyrimidine is used, whereby a compound having moderate gel properties can be obtained.

More amino groups in the side-chain amino silicone oil results in a harder gel. It is therefore preferred that the number of amino groups is proper. In order to obtain the soft gel-like product, the number of amino groups in the molecule is preferably 5 or less.

As described above, the hard gels, the soft gels and the liquid triazinyl group- or pyrimidinyl group-containing amino silicone derivatives are obtained according to various conditions, and they can be selected depending on each application, similarly to the above-mentioned various substituted compounds.

The novel triazinyl group- or pyrimidinyl group-containing amino silicone derivatives of the present invention are dispersed in liquid oil or silicone oil, and dissolved by heating, followed by cooling if necessary, thereby obtaining compositions extending from gel-like compositions to viscous materials.

The amount of the triazinyl group- or pyrimidinyl group-containing amino silicone derivative of the present invention added to the silicone oil varies with the molecular weight, etc. of the triazinyl group- or pyrimidinyl group-containing amino silicone derivative, and a higher molecular weight and a higher viscosity of the silicone derivative require a smaller amount thereof added. On the other hand, a lower molecular weight and a lower viscosity of the silicone derivative require a larger amount thereof added. In the latter case, the triazinyl group- or pyrimidinyl group-containing amino silicone derivative itself can also be used as a base. When used as a gelling agent, the triazinyl group- or pyrimidinyl group-containing amino silicone derivative of the present invention is added generally in an amount of 3% by weight or more, and preferably in an amount of 10% by weight or more. The gelling agent of the present invention also includes so-called viscosity thickening agents which increase the viscosity of the bases but leave the fluidity, as well as the so-called gelling which increases the viscosity and allows the fluidity to disappear.

The liquid oil may be any as long as it is compatible with the silicone derivatives of the present invention, and examples thereof include hydrocarbon oil such as isoparaffin oil, and ester oil. The silicone oil may be any as long as it is liquid, and chain silicones, cyclic silicones, amino-, carboxyl- or alcohol- silicones, etc. can be used.

The triazinyl group- or pyrimidinyl group-containing amino silicone derivatives of the present invention are dissolved in low-viscosity silicone oil, hydrocarbon oil, polar oil, etc. to cause gelation or an increase in viscosity. They can be therefore used as bases for various industrial materials as well as for cosmetics and pharmaceutical preparations. In addition, the triazinyl group- or pyrimidinyl group-containing amino silicone derivatives of the present invention themselves can be used as bases for cosmetics, pharmaceutical preparations and various industrial materials.

When, for example, silicone oil having a low viscosity of 100 cs or less generally used in cosmetics and pharmaceutical preparations is used as a soft, homogeneous gel, the use of the mono-substituted compound in which a triazinyl group or a pyrimidinyl group of the amino silicone is substituted provides a gel-like composition not impairing refreshing feeling of the silicone oil. When used as a hard, homogeneous gel high in form retention, the di-substituted compound is mainly employed.

As described above, when the silicone derivatives are used in cosmetics and pharmaceutical preparations, it is preferred that halogen is removed by substitution, etc.

The silicone oil is used for various industrial materials utilizing its insulating properties and water repellency, and can be used properly by various selections according to its purpose of use as a gelling agent.

The gel-like compositions comprising the triazinyl group- or pyrimidinyl group-containing amino silicone derivatives of the present invention and silicone oil are thermally reversible, and addition of DMSO to the gel-like compositions results in fluid liquids. From this fact, this gelation is deduced to be mainly caused by a hydrogen bond.

The present invention will be described in more detail with the following examples. It is understood of course that they are for the purpose of illustration only and are not intended to limit the scope of the invention.

EXAMPLE 1

Three grams ($1.2 \times 10^{-4}$ mol) of a side-chain amino silicone (BY16-849 manufactured by Dow Corning Toray Silicone Co., Ltd., MW: ca. 25000, amino equivalent: 600) dissolved in 20 g of benzene was mixed with 0.57 g ($5.0 \times 10^{-3}$ mol) of 2-chloropyrimidine previously dissolved in 20 g of benzene, and the mixture was stirred under reflux for 24 hours. After termination of the reaction, the solvent was removed by distillation under reduced pressure to obtain a 2-pyrimidinylorganopolysiloxane which has pyrimidinyl groups bound.

EXAMPLE 2

Thirty grams ($6.6 \times 10^{-3}$ mol) of a both-terminal amino silicone (BY16-853B manufactured by Dow Corning Toray Silicone Co., Ltd., MW: ca.4500, amino equivalent: 2250) dissolved in 15 g of benzene was mixed with 2.46 g ($13.3 \times 10^{-3}$ mol) of cyanuric chloride previously dissolved in 15 g of benzene, and the mixture was stirred at room temperature for 24 hours. After termination of reaction, the solvent was removed by distillation under reduced pressure, followed by washing with water. The resulting product was heated again under reduced pressure to remove the solvent by distillation, thereby mainly obtaining a triazinylorganopolysiloxane in which triazinyl groups were bound to both ends. This product showed the following nuclear magnetic resonance spectra:

TABLE 1

Structure Confirmation According to Nuclear Magnetic Resonance Spectra ($^{13}$C-NMR)

| Structure | Chemical Shift δ |
|---|---|
| $\overset{\text{II}}{\underset{\text{T}}{C}}$—NH—R—Si(R)₃ | 166.1 ppm |
| $\overset{\text{II}}{\underset{\text{T}}{C}}$—Cl | 169.9 ppm<br>171.1 ppm |

Solvent: CDCl₃

EXAMPLE 3

3.1 g ($1.24 \times 10^{-4}$ mol) of a side-chain amino silicone (BY16-849 manufactured by Dow Corning Toray Silicone Co., Ltd., MW: ca.25000, amino equivalent: 600) dissolved in 50 g of 1,4-dioxane was mixed with 0.1 g ($4.95 \times 10^{-4}$ mol) of 2-chloro-4,6-bis(ethylamino)-s-triazine previously dissolved in 50 g of 1,4-dioxane, and the mixture was stirred under reflux at the boiling point for 24 hours. After termination of the reaction, the solvent was removed by distillation under reduced pressure to mainly obtain a 2-[4,6-bis (ethylamino)]-s-triazinylorganopoly-siloxane in which 2-chloro-4,6-bis(ethylamino)-s-triazinyl groups were bound to a part of amino groups of one molecule of the side-chain amino silicone. This product showed the following nuclear magnetic resonance spectra:

TABLE 2

Structure Confirmation According to Nuclear Magnetic Resonance Spectra ($^{13}$C-NMR)

| Structure | Chemical Shift δ |
|---|---|
| —CH₃ (of an aminoethyl group) | 15 ppm |
| —CH₂— (of an aminoethyl group) | 35 ppm |
| $\overset{\text{II}}{\underset{\text{T}}{C}}$—NH—R—Si(R)₃<br>(carbon of a triazinyl ring to which a silicone was bound) | 163 ppm |
| $\overset{\text{II}}{\underset{\text{T}}{C}}$—NH—CH₂—CH₃<br>(carbon of a triazinyl ring to which an aminoethyl group was bound) | 165 ppm |

Solvent: CDCl₃

EXAMPLE 4

11.19 g ($2.48 \times 10^{-3}$ mol) of an α,ω-diamino silicone (BY16-843B manufactured by Dow Corning Toray Silicone Co., Ltd., MW: ca.4500, amino equivalent: 2250) dissolved in 150 g of 1,4-dioxane was mixed with 1 g ($4.95 \times 10^{-3}$ mol) of 2-chloro-4,6-bis(ethylamino)-s-triazine previously dissolved in 150 g of 1,4-dioxane, and the mixture was refluxed for 24 hours with stirring at 90° C. After termination of the reaction, the solvent was removed by distillation under reduced pressure to obtain a 2-[4,6-bis(ethylamino)]-s-triazinylorganopolysiloxane in which 2-chloro-4,6-bis (ethylamino)-s-triazinyl groups were bound to both ends. This compound was highly viscous and paste-like.

EXAMPLE 5

0.22 g ($1.19 \times 10^{-3}$ mol) of cyanuric chloride dissolved in 20 g of benzene was mixed with 5.0 g ($1.11 \times 10^{-3}$ mol) of silicone oil having one amino end group (MW: ca. 4500), followed by stirring for 24 hours. After termination of the reaction, the solvent was removed by distillation under reduced pressure to mainly obtain a triazinylorganopoly-siloxane in which one silicone chain was bound to a triazinyl group.

EXAMPLE 6

0.11 g ($0.59 \times 10^{-3}$ mol) of cyanuric chloride dissolved in 20 g of benzene was mixed with 5.0 g ($1.11 \times 10^{-3}$ mol) of silicone oil having one amino end group, BX16-193, followed by stirring for 24 hours. After termination of the reaction, the solvent was removed by distillation under reduced pressure to mainly obtain a triazinylorganopolysi-loxane in which two silicone chains were bound to a triazine compound.

EXAMPLE 7

0.07 g ($0.37 \times 10^{-3}$ mol) of cyanuric chloride dissolved in 20 g of benzene was mixed with 5.0 g ($1.11 \times 10^{-3}$ mol) of silicone oil having one amino end group, BX16-193, followed by stirring for 24 hours. After termination of the reaction, the solvent was removed by distillation under reduced pressure to mainly obtain a triazinylorganopolysiloxane in which three silicone chains were bound to a triazine compound.

EXAMPLE 8

Amino silicone derivatives (1) to (7) obtained in Examples 1 to 7 were each added to respective silicones so as to give a concentration of 10% by weight or 20% by weight, and dissolved by heating at room temperature or 80° C. with stirring. The resulting solutions were each allowed to stand at room temperature, followed by observation. The gelling and viscosity increasing properties of the derivatives obtained in Examples 1 to 7 to the silicones are shown below.

TABLE 3

| Sample | Concentration (%) | Silicone No. 1 | No. 2 | No. 3 |
| --- | --- | --- | --- | --- |
| Example 1 | 10 | Δ | Δ | Δ |
|  | 20 | o | o | o |
| Example 2 | 10 | ⊚ | ⊚ | ⊚ |
|  | 20 | ⊚ | ⊚ | ⊚ |
| Example 3 | 10 | Δ | Δ | Δ |
|  | 20 | Δ | Δ | Δ |
| Example 4 | 10 | Δ | Δ | Δ |
|  | 20 | Δ | Δ | Δ |
| Example 5 | 10 | o | ⊚ | Δ |
|  | 20 | o | ⊚ | Δ |
| Example 6 | 10 | ⊚ | ⊚ | ⊚ |
|  | 20 | ⊚ | ⊚ | ⊚ |
| Example 7 | 10 | o | o | Δ |
|  | 20 | o | o | Δ |

No. 1: dimethylpolysiloxane 5 cs
No. 2: dimethylpolysiloxane 50 cs
No. 3: decamethylcyclopentasiloxane 5 cs
⊚: gel (form retention kept)
o: weak gel
Δ: increase in viscosity
x: solution The equivalent amount of DMSO was added to each gel of No. 1 obtained in Example 1, 2, 5, 6 or 7 shown in Table 3, followed by stirring. As a result, each gel was turned solution-like. From this fact, this gel was deduced to be mainly made by a hydrogen bond.

The novel silicone derivatives of the present invention can be easily synthesized from the amino silicones and the triazine or pyrimidine compounds, and can gel silicone oil or increase the viscosity thereof stably and homogeneously. The gelled products are thermally reversible, and easily produced. Further, the resulting gels are transparent. The reason for this is deduced to be that this gel is mainly made by a hydrogen bond.

What is claimed is:

1. A compound represented by the formula:

wherein at least one X is $$-N-(CH_2)_m-\left[-N-(CH_2)_n-\right]_h\left(\begin{array}{c}R\\|\\Si-O\\|\\R\end{array}\right)_a\begin{array}{c}R\\|\\Si-B\\|\\R\end{array}$$

and each remaining X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, and alkoxy having 1 to 6 carbon atoms;

each R, which may be the same or different, represents hydrogen or a linear, branched-chain or cyclic hydrocarbon group of 1 to 8 carbon atoms; m, n and h each represents integers from 1 to 6; "a" represents an integer from 1 to 400; and wherein B is R or 2. A compound according to claim 1, represented by the general formula:

(2)

wherein R, m, n, h, and "a" have the same meaning as given previously; Y is a nitrogen atom; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, or as well a hydrogen atom, is bound to a residual carbon atom of the triazine ring.

3. A compound represented by general formula (3):

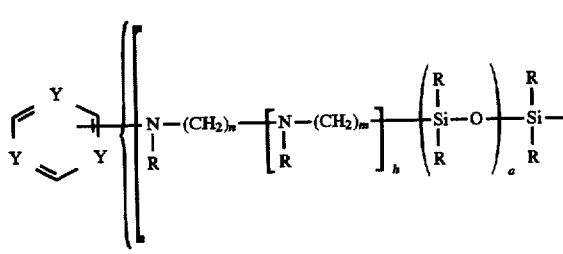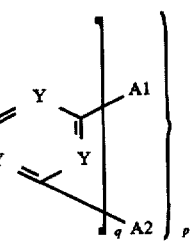

(3)

wherein each R, which may be the same or different, represents hydrogen or a linear, branched-chain or cyclic hydrocarbon group of 1 to 8 carbon atoms; m, n and h each represent integers from 1 to 6; "a" represents an integer from 1 to 400; Y is nitrogen; q represents an integer from 0 to 10; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, or as well a hydrogen atom, is bound to a residual carbon atom of the triazine ring; and (i) when q is from 1 to 10, A1 and A2 are each represented by general formula (4):

linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms; and (ii) when q is 0, general formula (3) is represented by general formula (6):

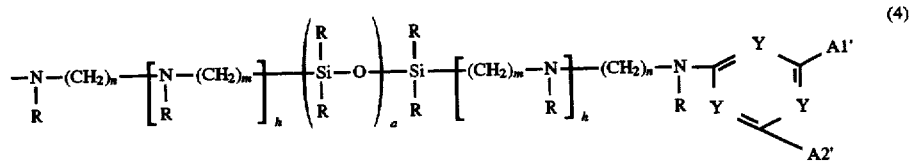

(4)

wherein R, m, n, h, a and Y have the same meanings as given above, and A1' and A2' each represents hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms;

or A1 and A2 are each represented by general formula (5):

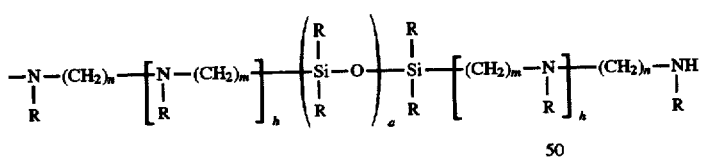

(5)

wherein R, m, n, h and "a" have the same meanings as given above;

or A1 and A2 each represent hydrogen atoms, hydroxyl groups, amino groups which may be substituted by

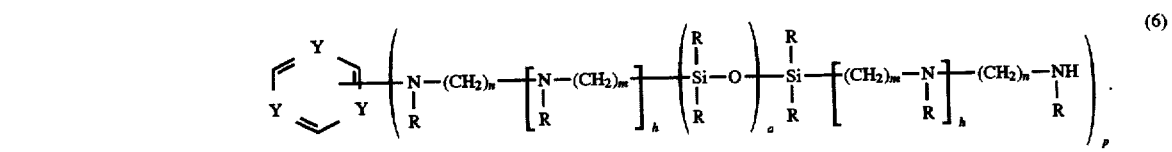

(6)

4. A compound represented by the following general formula which is obtained by allowing a side-chain amino silicone to react with a reactive group-containing triazine compound:

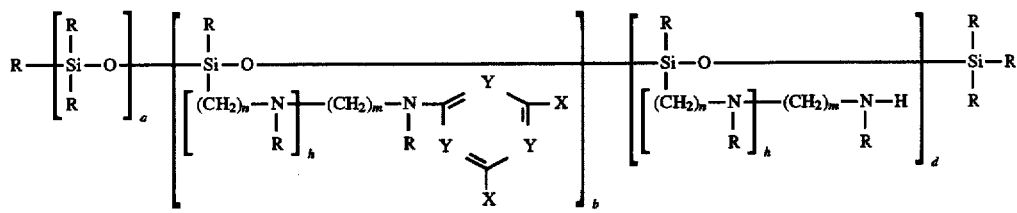

wherein each R, which may be the same or different, represents hydrogen or a linear, branched-chain or cyclic hydrocarbon group of 1 to 8 carbon atoms; m, n and h each represent integers from 1 to 6; "a" and "b" each represent integers of 1 or more, "d" represents an integer of 0 or more, and "a+b+d" represents an integer of 400 or less; and "a", "b" and "d" each show the relative number but do not specify the order of arrangement; and wherein each X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, alkoxy having 1 to 6 carbon atoms, and

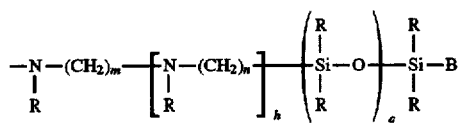

wherein B is R or

5. A method for producing a compound according to claim 1, the method comprising reacting with a reactive group-containing triazine or pyrimidine compound an amino silicone oil represented by the following general formula (8):

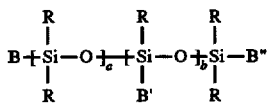

(8)

wherein each R, which may be the same or different, represents hydrogen or a linear, branched-chain or cyclic hydrocarbon group of 1 to 8 carbon atoms; "a" and "b" each represent integers of 1 or more, and the sum of "a" and "b" represents an integer of 400 or less; "a" and "b" each show the relative number but do not specify the order of arrangement; and at least one of B, B' and B" is a group represented by general formula (9):

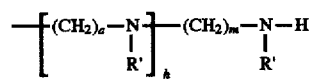

(9)

wherein each R', which may be the same or different, represents hydrogen or a linear, branched or cyclic hydrocarbon group of 1 to 8 carbon atoms; m, n and h each represent integers from 1 to 6; and the reactive group-containing triazine compound is a compound represented by the following general formula:

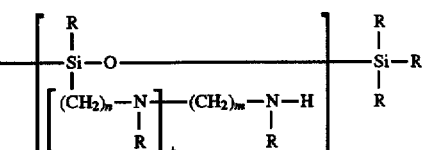

wherein at least one of X represents a halogen atom, and each remaining X represents a hydrogen atom, a hydroxyl group, an amino group which may be substituted by linear or branched alkyl groups each having 1 to 6 carbon atoms, a carboxyl group, a linear or branched alkyl group having 1 to 6 carbon atoms, or a linear or branched alkoxyl group having 1 to carbon atoms.

6. A composition comprising an admixture of (i) a compound and (ii) a liquid oil or silicone oil, said compound represented by the formula:

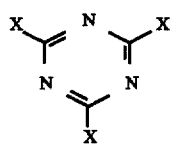

wherein at least one X is

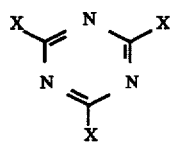

and each remaining X is independently selected from the group consisting of hydrogen, halogen, hydroxyl, amino which may be substituted by linear or branched alkyl groups each having 1 to 6 carbon atoms, carboxyl, alkyl having 1 to 6 carbon atoms, and alkoxy having 1 to 6 carbon atoms;

each R, which may be the same or different, represents hydrogen or a linear, branched-chain or cyclic hydrocarbon group of 1 to 8 carbon atoms; m and n each represents integers from 1 to 6; h represents integers from 0 to 6; "a" represents an integer from 1 to 400; and wherein B is R or

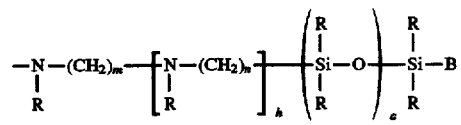

7. The composition according to claim 6, wherein said compound is represented by the general formula:

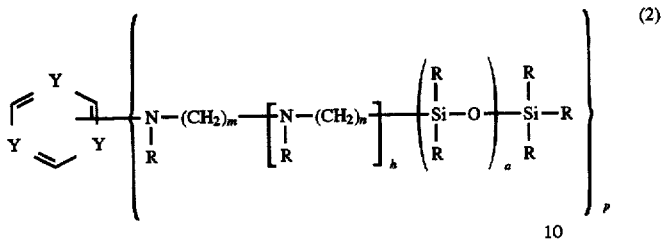

wherein R, m, n, h, and "a" have the same meaning as given previously; Y is a nitrogen atom; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkoxyl group of 1 to 6 carbon atoms, or a linear or branched alkoxyl group of 1 to 6 carbon atoms, or as well a hydrogen atom, is bound to a residual carbon atom of the triazine ring.

8. The composition according to claim 6, wherein said compound represented by general formula (3):

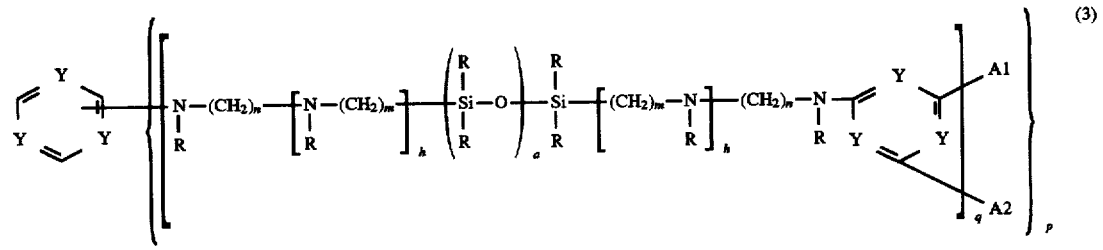

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" represents an integer from 1 to 400; Y is nitrogen; q represents an integer from 0 to 10; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, or as well a hydrogen atom, is bound to a residual carbon atom of the triazine ring; and (i) when q is from 1 to 10, A1 and A2 are each represented by general formula (4):

wherein R, m, n, h, a and Y have the same meanings as given above, and A1' and A2' each represents hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms;

or A1 and A2 are each represented by general formula (5):

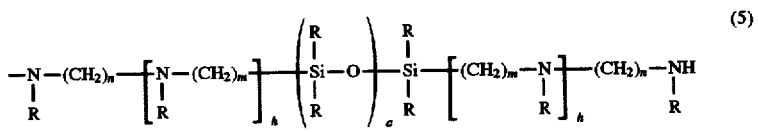

wherein R, m, n, h and "a" have the same meanings as given above; or A1 and A2 each represent hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms; and

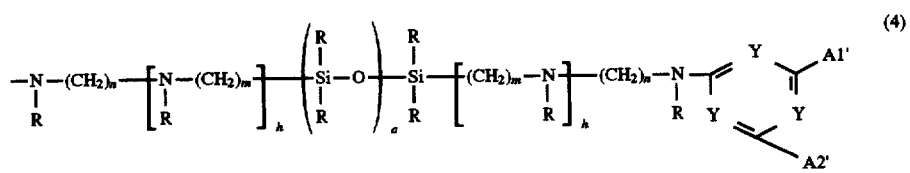

(ii) when q is 0, general formula (3) is represented by general formula (6):

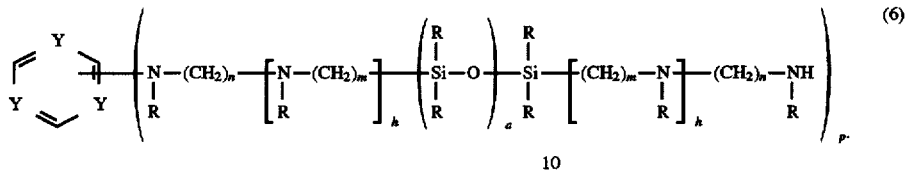 (6)

9. The composition according to claim 6, wherein said compound is represented by the following formula which is obtained by allowing a side-chain amino silicone to react with a reactive group-containing triazine compound:

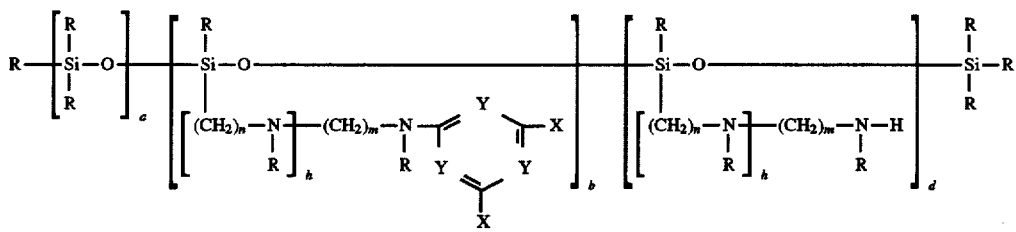

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" and "b" each represent integers of 1 or more, "d" represents an integer of 0 or more, and "a+b+d" represents an integer of 400 or less; and "a", "b" and "d" each show the relative number but do not specify the order of arrangement; and wherein each X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, alkoxy having 1 to 6 carbon atoms, and

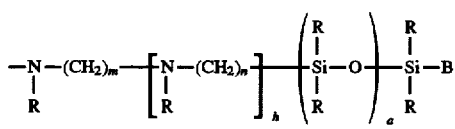

wherein B is R or

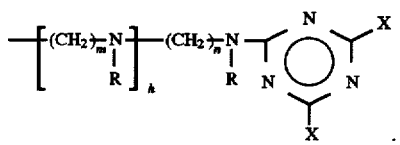

10. A gel comprising an admixture of (i) a compound and (ii) a liquid oil or silicone oil, said compound represented by the formula:

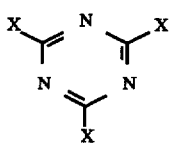

wherein at least one X is

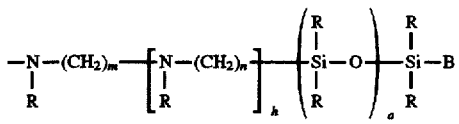

and each remaining X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, and alkoxy having 1 to 6 carbon atoms;

each R, which may be the same or different, represents hydrogen or a linear, branched-chain or cyclic hydrocarbon group of 1 to 8 carbon atoms; m and n each represents integers from 1 to 6; h represents integers from 0 to 6; "a" represents an integer from 1 to 400; and wherein B is hydrogen, R or

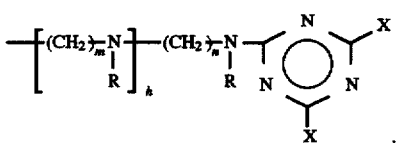

11. The gel according to claim 10, wherein said compound is represented by the general formula:

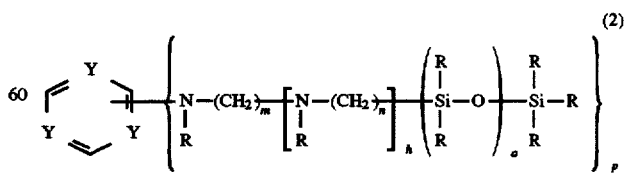 (2)

wherein R, m, n, h, and "a" have the same meaning as given previously; Y is a nitrogen atom; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkoxyl group of 1 to 6 carbon atoms, or a linear or branched alkoxyl group of 1 to 6 carbon atoms, or as well a hydrogen atom, is bound to a residual carbon atom of the triazine ring.

12. The gel according to claim 10, wherein said compound represented by general formula (3):

or A1 and A2 each represent hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms; and

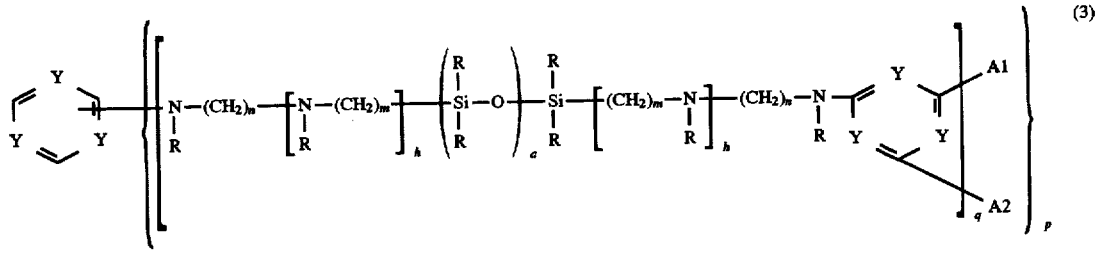

(3)

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" represents an integer from 1 to 400; Y is nitrogen; q represents an integer from 0 to 10; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, or as well a hydrogen atom, is bound to a residual carbon atom of the triazine ring; and (i) when q is from 1 to 10, A1 and A2 are each represented by general formula (4):

(ii) when q is 0, general formula (3) is represented by general formula (6):

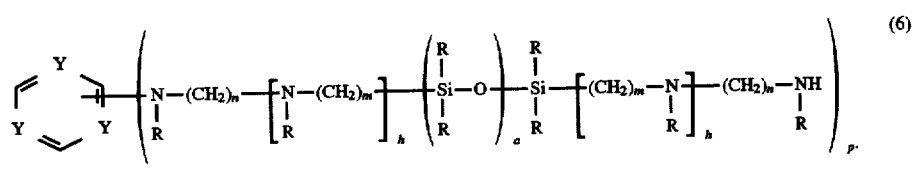

(6)

13. The gel according to claim 10, wherein said compound is represented by the following formula, which is obtained by allowing a side-chain amino silicone to react with a reactive group-containing triazine compound:

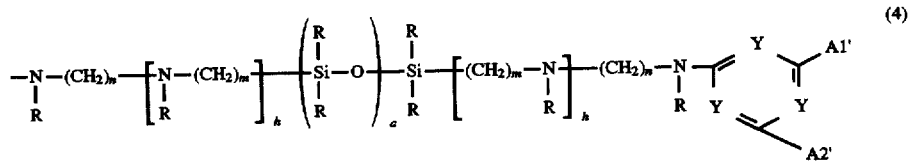

(4)

wherein R, m, n, h, a and Y have the same meanings as given above, and A1' and A2' each represents hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms;

or A1 and A2 are each represented by general formula (5):

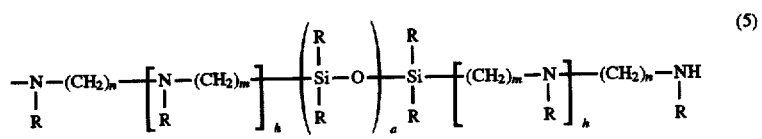

(5)

wherein R, m, n, h and "a" have the same meanings as given above;

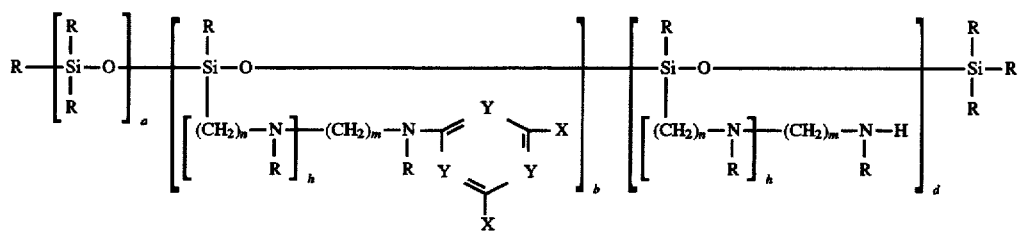

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" and "b" each represent integers of 1 or more, "d" represents an integer of 0 or more, and "a+b+d" represents an integer of 400 or less; and "a", "b" and "d" each show the relative number but do not specify the order of arrangement; and wherein each X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, alkoxy having 1 to 6 carbon atoms, and

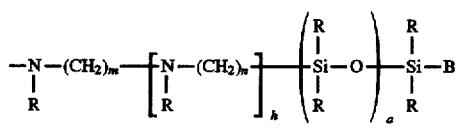

wherein B is R or

14. A base for a cosmetic or a pharmaceutical preparation, the base comprising an admixture of (i) a compound and (ii) a liquid oil or silicone oil, said compound represented by the formula:

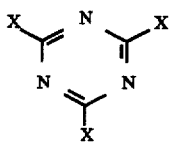

wherein at least one X is

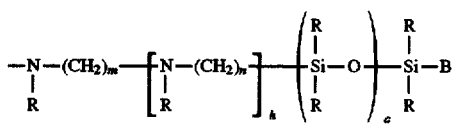

and each remaining X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, and alkoxy having 1 to 6 carbon atoms;

each R, which may be the same or different, represents hydrogen or a linear, branched-chain or cyclic hydrocarbon group of 1 to 8 carbon atoms; m and n each represents integers from 1 to 6; h represents integers from 0 to 6; "a" represents an integer from 1 to 400; and wherein B is R or

15. The base according to claim 14, wherein said compound is represented by the general formula:

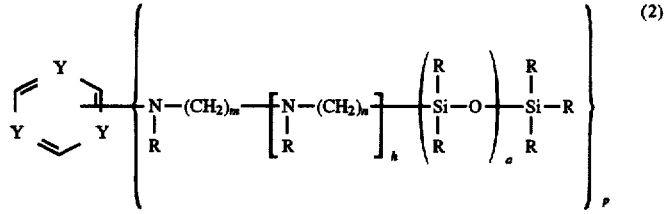

(2)

wherein R, m, n, h, and "a" have the same meaning as given previously; Y is a nitrogen atom; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkoxyl group of 1 to 6 carbon atoms, or a linear or branched alkoxyl group of 1 to 6 carbon atoms, or as well a hydrogen atom, is bound to a residual carbon atom of the triazine ring.

16. The base according to claim 14, wherein said compound represented by general formula (3):

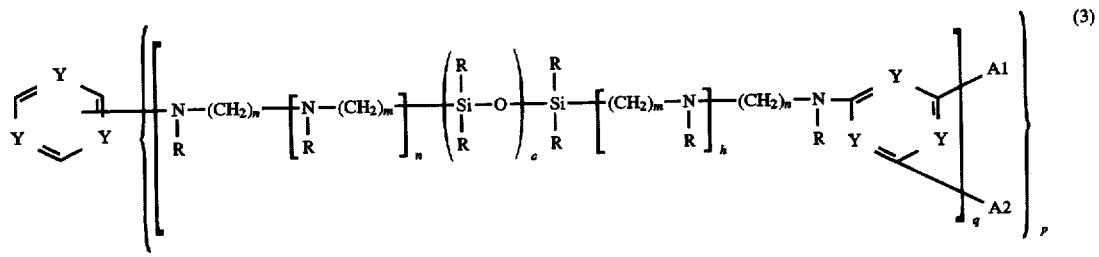

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" represents an integer from 1 to 400; Y is nitrogen; q represents an integer from 0 to 10; p represents an integer from 1 to 3; and, when p is 1 or 2, a hydroxyl group, an amino group which may be substituted by a linear or branched alkyl group of 1 to 6 carbon atoms, a halogen atom, a carboxyl group, a linear or branched alkyl group of 1 to 6 carbon atoms, or a linear or branched alkoxyl group of 1 to 6 carbon atoms, or as well a hydrogen atom, is bound to a residual carbon atom of the triazine ring; and (i) when q is from 1 to 10, A1 and A2 are each represented by general formula (4):

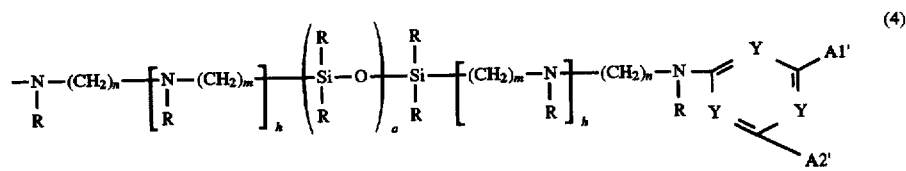

wherein R, m, n, h, a and Y have the same meanings as given above, and A1' and A2' each represents hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms;

or A1 and A2 are each represented by general formula (5):

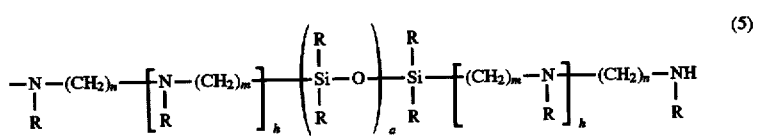

wherein R, m, n, h and "a" have the same meanings as given above;

or A1 and A2 each represent hydrogen atoms, hydroxyl groups, amino groups which may be substituted by linear or branched alkyl groups each having 1 to 6 carbon atoms, halogen atoms, carboxyl groups, linear or branched alkyl groups each having 1 to 6 carbon atoms, or linear or branched alkoxyl groups each having 1 to 6 carbon atoms; and (ii) when q is 0, general formula (3) is represented by general formula (6):

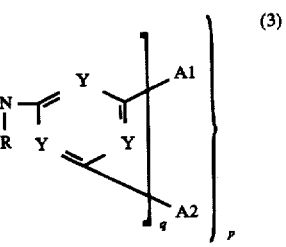

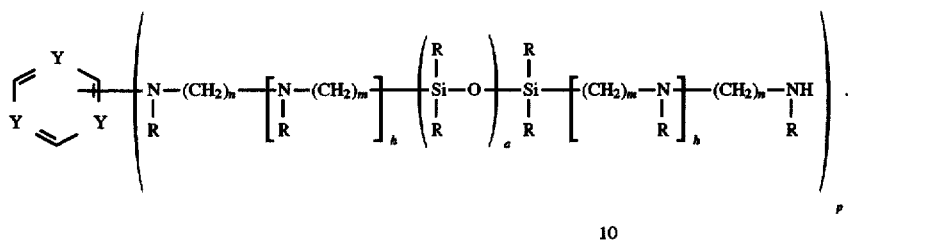

17. The base according to claim 14, wherein said compound is represented by the following formula, which is obtained by allowing a side-chain amino silicone to react with a reactive group-containing triazine compound:

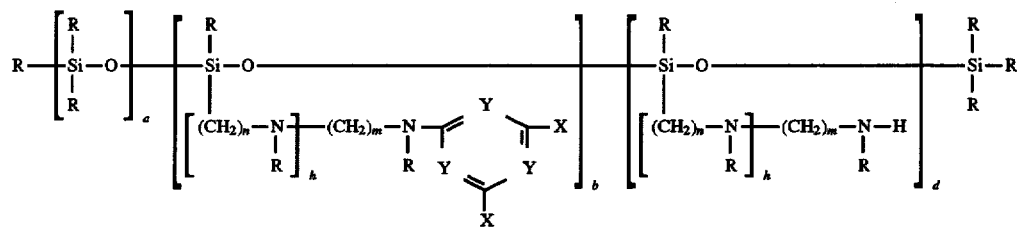

wherein each R, which may be the same or different, represents hydrogen or a linear, branched-chain or cyclic hydrocarbon group of 1 to 8 carbon atoms; m and n each represent integers from 1 to 6; h represent integers from 0 to 6; "a" and "b" each represent integers of 1 or more, "d" represents an integer of 0 or more, and "a+b+d" represents an integer of 400 or less; and "a", "b" and "d" each show the relative number but do not specify the order of arrangement; and wherein each X is independently selected from the group consisting of hydrogen, halogen, hydroxyl, amino which may be substituted by a linear or branched alkyl group of 1 to 6 carbon atoms, carboxyl, alkyl having 1 to 6 carbon atoms, alkoxy having 1 to 6 carbon atoms, and

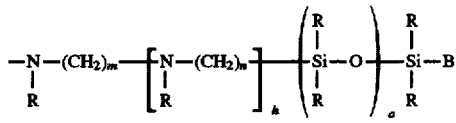

wherein B is R or

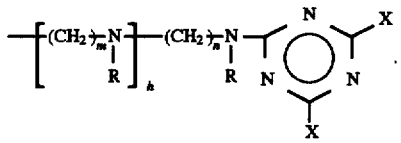

\* \* \* \* \*